(12) United States Patent
Sakata et al.

(10) Patent No.: US 10,488,317 B2
(45) Date of Patent: Nov. 26, 2019

(54) METHOD OF EVALUATING AMOUNT OF FOREIGN MATTER PASSED THROUGH RECIRCULATION SUMP SCREEN

(71) Applicant: Mitsubishi Heavy Industries, Ltd., Tokyo (JP)

(72) Inventors: Hideyuki Sakata, Tokyo (JP); Hiroyuki Kojima, Tokyo (JP); Hiroshi Matsuoka, Tokyo (JP); Yuji Momose, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 330 days.

(21) Appl. No.: 15/375,346

(22) Filed: Dec. 12, 2016

(65) Prior Publication Data

US 2017/0176315 A1 Jun. 22, 2017

(30) Foreign Application Priority Data

Dec. 22, 2015 (JP) ................................. 2015-250559

(51) Int. Cl.
| | |
|---|---|
| *G01N 15/08* | (2006.01) |
| *G21C 15/18* | (2006.01) |
| *G21C 17/022* | (2006.01) |
| *G21C 19/307* | (2006.01) |

(52) U.S. Cl.
CPC ....... *G01N 15/0806* (2013.01); *G21C 15/182* (2013.01); *G21C 17/022* (2013.01); *G21C 19/307* (2013.01); *G01N 2015/084* (2013.01); *Y02E 30/40* (2013.01)

(58) Field of Classification Search
CPC ......... G01N 15/0806; G01N 2015/084; G21C 19/307; G21C 17/022; G21C 15/182; Y02E 30/40
See application file for complete search history.

(56) References Cited

U.S. PATENT DOCUMENTS

2013/0108509 A1* 5/2013 Shiba .................... G01N 21/51
422/82.05

FOREIGN PATENT DOCUMENTS

| EP | 1 559 467 B1 | | 1/2006 |
|---|---|---|---|
| JP | 2011-13103 A | | 1/2011 |
| KR | 20120025105 A | * | 3/2012 |

* cited by examiner

*Primary Examiner* — Justin Seo
*Assistant Examiner* — John M Royston
(74) *Attorney, Agent, or Firm* — Westerman, Hattori, Daniels & Adrian, LLP (57) ABSTRACT

Acquiring sets of test data on amounts of foreign matter passed through a recirculation sump screen when different amounts of foreign matter are input; forming a passed foreign matter amount approximate line that approximates the amounts of passed foreign matter with respect to the amounts of input foreign matter on the basis of the sets of test data on the amounts of passed foreign matter; forming a passed foreign matter amount envelope tangent to the passed foreign matter amount approximate line; and estimating a total passed foreign matter amount with respect to the amounts of input foreign matter on the basis of the passed foreign matter amount envelope to evaluate the recirculation sump screen are provided.

7 Claims, 4 Drawing Sheets

METHOD OF EVALUATING AMOUNT OF FOREIGN MATTER PASSED THROUGH RECIRCULATION SUMP SCREEN

FIELD

The present invention relates to a method of evaluating an amount of foreign matter passed through a recirculation sump screen that is used in a system that circulates a coolant in a containment when a loss-of-coolant accident occurs in a reactor.

BACKGROUND

For example, a nuclear power plant including a pressurized water reactor (PWR) uses light water as a reactor coolant and a neutron moderator, which is light water serving as a high-temperature and high-pressure water that does not boil over the reactor internal of the reactor, sends the high-temperature and high-pressure water to a steam generator to generate steam by heat exchange, and sends the steam to a turbine generator to generate power. The steam generator transmits the heat of a primary cooling water with a high temperature and a high pressure from the reactor to a secondary cooling water to generate steam with the secondary cooling water.

In such a nuclear power plant, when a loss-of-coolant accident occurs due to a break of a pipe in the reactor, it becomes difficult to sufficiently cool the reactor with the coolant. For this reason, the reactor is cooled urgently by pumping up the cooling water in a refueling water storage pit with a pump, supplying the cooling water into the reactor, spraying the cooling water toward the reactor from multiple spray nozzles that are arranged at an upper part of the containment. In this case, foreign matter caused due to the break of the pipe falls into the refueling water storage pit and, for this reason, a recirculation sump screen is placed on the top of the refueling water storage pit. Accordingly, the foreign matter is blocked by the recirculation sump screen to inhibit the foreign matter from entering the refueling water storage pit, which prevents the pumps and pipes from being damaged due to the foreign matter.

Note that there is the device according to the following Patent Document 1 as a reactor emergency cooling device.

CITATION LIST

Patent Literature

Patent Literature 1: Patent Document 1: Japanese Laid-open Patent Publication No. 2011-013103

SUMMARY

Technical Problem

The above-described recirculation sump screen filters out foreign matter to prevent the foreign matter from entering the facility on the downstream side with respect to the screen; however, small foreign matter passes through (is not filtered out by) the recirculation sump screen. For this reason, it is necessary to evaluate in advance how much foreign matter passes through the recirculation sump screen when an accident occurs. In the containment, however, multiple refueling water storage pits are provided. It is difficult to uniquely determine how much foreign matter is transferred to each recirculation sump screen as it depends on multiple parameters, such as the position of the break of the pipe and the state of damage of the foreign matter. In other words, it is difficult to evaluate the amount of foreign matter that reaches each recirculation sump screen and the amount of the passed foreign matter and then quantitatively calculate the total amount of the passed foreign matter.

The present invention is aimed at solving the above-described problem and an objective of the present invention is to provide a method of evaluating an amount of foreign matter passed through a recirculation sump screen enables easy calculation of a total amount of foreign matter passed through multiple recirculation sump screens.

Solution to Problem

To achieve the above-described object, a method of evaluating an amount of foreign matter passed through a recirculation sump screen according to an present invention includes acquiring sets of test data on amounts of foreign matter passed through a recirculation sump screen when different amounts of foreign matter are input, forming a passed foreign matter amount approximate line that approximates the amounts of passed foreign matter with respect to the amounts of input foreign matter on the basis of the sets of test data on the amounts of passed foreign matter, forming a passed foreign matter amount envelope tangent to the passed foreign matter amount approximate line, and calculating a total amount of passed foreign matter with respect to the amounts of input foreign matter on the basis of the passed foreign matter amount envelope to evaluate the recirculation sump screen.

Accordingly, the passed foreign matter amount approximate line is formed on the basis of the multiple sets of test data on the amounts of passed foreign matter, the passed foreign matter amount envelope tangent to the passed foreign matter amount approximate line is formed, and the total amount of passed foreign matter with respect to the input foreign matter amount is calculated on the basis of the passed foreign matter amount envelope to evaluate the recirculation sump screen. Accordingly, it is possible to calculate the total amount of passed foreign matter easily and evaluate the recirculation sump screen accurately, without individually evaluating the amounts of foreign matter reaching the multiple recirculation sump screens and the passed foreign matter amounts and without necessity of calculating a ratio of the passed foreign matter.

In the method of evaluating the amount of foreign matter passed through the recirculation sump screen according to the present invention, the passed foreign matter amount approximate line is a quadratic curve and the passed foreign matter amount envelope is a primary expression straight line.

The passed foreign matter amount approximate line is a quadratic curve and the passed foreign matter amount envelope is a primary expression straight line and accordingly it is possible to calculate the total amount of passed foreign matter accurately according to the single simple expression.

The method of evaluating the amount of foreign matter passed through the recirculation sump screen according to the present invention includes forming a passed foreign matter amount approximate straight line on the basis of the passed foreign matter amount approximate line and forming the passed foreign matter amount envelope on the basis of the passed foreign matter amount approximate straight line.

Forming the passed foreign matter amount approximate straight line on the basis of the passed foreign matter amount approximate line and forming the passed foreign matter amount envelope thus make it possible to calculate an average ratio of the passed foreign matter between the multiple recirculation sump screens and calculate a total passed foreign matter amount easily.

In the method of evaluating the amount of foreign matter passed through the recirculation sump screen according to the present invention, a passed foreign matter amount envelope is set in a shifted area defined by the passed foreign matter amount envelope tangent to the passed foreign matter amount approximate line and a passed foreign matter amount envelope shifted to a pre-set side where the passed foreign matter amount increases.

The passed foreign matter amount envelope in the shifted area moved to the side where the passed foreign matter amount increases is set such that a sufficient factor of safety is secured.

In the method of evaluating the amount of foreign matter passed through the recirculation sump screen according to the present invention, the shifted area is an area moved to a side where the amount of passed foreign matter is smaller than a maximum value of the sets of test data on the amounts of passed foreign matter.

The shifted area is the area moved to the side where the amount of passed foreign matter is smaller than the maximum value of the sets of test data on amounts of passed foreign matter, and thus the efficiency in processing can be improved without securing an excessive factor of safety.

Advantageous Effects of Invention

According to the method of evaluating an amount of foreign matter passed through a recirculation sump screen according to the present invention, the passed foreign matter amount approximate line is formed on the basis of the multiple sets of test data on the amounts of passed foreign matter, the passed foreign matter amount envelope tangent to the passed foreign matter approximate line is formed, and the total passed foreign mater amount with respect to the input foreign matter amount is calculated on the basis of the passed foreign matter amount envelope to evaluate the recirculation sump screen, and accordingly it is possible to calculate the total passed foreign matter amount easily and evaluate the recirculation sump screen accurately.

DESCRIPTION OF EMBODIMENTS

With reference to the accompanying drawings, a preferred embodiment of the method of evaluating an amount of foreign matter passed through a recirculation sump screen according to the present invention will be described in detail below. The embodiment does not limit the invention. If there are multiple embodiments, the invention will cover ones configured by combining the embodiments.

First Embodiment

Figure 1:
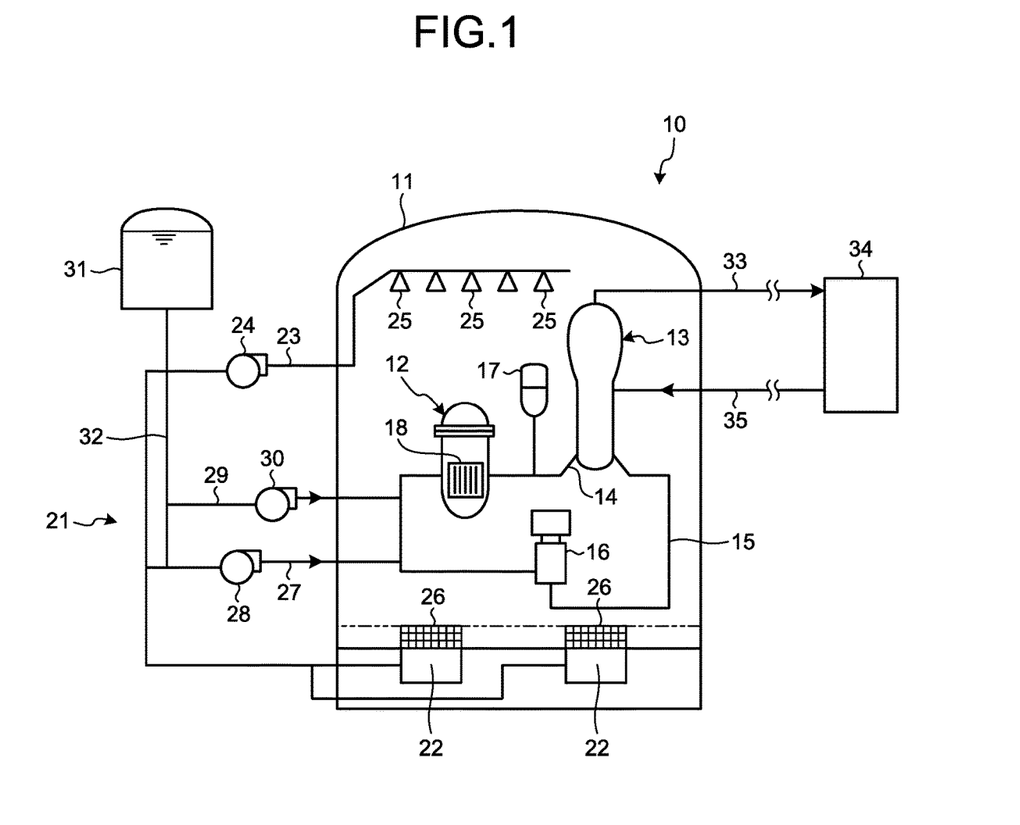
FIG. 1 is a schematic configuration diagram illustrating a main part of a nuclear power plant.

FIG. 1 is a schematic configuration diagram illustrating a main part of a nuclear power plant.

In the present embodiment, a nuclear power plant includes a reactor. The reactor is a pressurized water rector (PWR) that uses light water as a reactor coolant and a neutron moderator, which is light water serving as a high-temperature and high-pressure water that does not boil over the reactor internal, sends the high-temperature and high-pressure water to a steam generator to generate steam by heat exchange, and sends the steam to a turbine generator to generate power. The reactor may be a boiling water reactor (BWR).

As shown in FIG. 1, in a nuclear power plant 10, a PWR 12 and multiple steam generators 13 (one steam generator is illustrated) are stored in a containment 11. The PWR 12 and each of the steam generators 13 are connected via a high-temperature feeding pipe 14 and a low-temperature feeding pipe 15, and a primary cooling water pump 16 is provided on the low-temperature feeding pipe 15. The bottom of a pressurizer 17 is connected to the high-temperature feeding pipe 14.

In the PWR 12, a reactor internal 18 is arranged. The reactor internal 18 consists of multiple fuel assemblies (fuel rods) (not illustrated). Although it is not illustrated, multiple control rods are arranged between the fuel assemblies in the reactor internal 18 and the control rods can be moved vertically by a control rod driver device. Inserting the control rods into the reactor internal 18 and extracting the control rods from the reactor internal 18 enables control on the output of the reactor.

In the steam generator 13, heat transmission pipe group consisting of multiple heat transmission pipes having the inversed shape of the shape of U are arranged, one end of each of the heat transmission pipe is connected to an end of the high-temperature feeding pipe 14 and the other end is connected to an end of the low-temperature feeding pipe 15.

In the containment 11, a reactor emergency cooling device 21 is provided. Multiple refueling water storage pits 22 are provided at the bottom of the containment 11 and a cooling water dispersion line 23 that returns from each of the refueling water storage pits 22 into the containment 11 through the outside of the containment 11 and extends above the PWR 12 is provided. The cooling water dispersion line 23 has a middle part where a spray pump 24 is provided and has a tip where a large number of spray nozzles 25 are provided. A recirculation sump screen 26 is placed on each of the refueling water storage pits 22 to cover the top of the refueling water storage pit 22.

A low-pressure cooling water supply line 27 is a low-pressure water feeding system that returns from the refueling water storage pits 22 into the containment 11 through the outside of the containment 11, that is connected to the PWR 12, and that is provided with a low-pressure injection pump 28 is provided. A high-pressure cooling water supply line 29 is a high-pressure water supply system that returns from the refueling water storage pits 22 into the containment 11 through the outside of the containment 11, that is connected to the PWR 12, and that is provided with a high-pressure injection pump 30. A fuel replacement water tank 31 is arranged outside the containment 11 and is connected to the cooling water dispersion line 23, the low-pressure cooling water supply line 27, and the high-pressure cooling water supply line 29 via a cooling water supply line 32.

In the PWR 12, the fuel assemblies in the reactor internal 18 heat the light water serving as the primary cooling water and, in a state where the primary cooling water at a high temperature is kept at a given high pressure by the pressurizer 17, the primary cooling water is sent to the steam generator 13 through the high-temperature feeding pipe 14. The steam generator 13 generates secondary steam by performing heat exchange between the primary cooling water at a high-temperature and a high-pressure and the secondary cooling water, and the cooled primary cooling water is returned to the PWR 12. The control rod driver device adjusts the nuclear fission in the reactor internal 18 by extracting the control rods from the reactor internal 18 and inserting the control rods into the reactor internal 18. By inserting all the control rods into the reactor internal 18, the control rod driver device is able to stop the PWR 12.

Each of the steam generators 13 has a top end that is connected to a power generation facility 34 via a steam supply pipe 33, and the power generation facility 34 is connected to the steam generator 13 via a condensed water return pipe 35. The power generation facility 34 consists of a steam turbine facility, a power generator, a condenser, etc. In the steam generator 13, the secondary steam that is generated by performing heat exchange between the secondary cooling water and the primary cooling water at a high temperature and a high pressure is sent to the steam turbine of the power generation facility 34 via the steam supply pipe 33, and the steam drives the steam turbine to generate power with the power generator. The condenser uses sea water to cool the steam having driven the steam turbine and generate the condensed water, and the condensed water is returned to the steam generator 13 through the condensed water return pipe 35.

When an accident of a break of the cooling pipe occurs in the nuclear power plant 10, the spray pump 24 is driven to send the primary cooling water stored in each of the refueling water storage pits 22 to the large number of spray nozzles 25 via the primary cooling water dispersion line 23 and the primary cooling water is dispersed from the large number of spray nozzles 25 to the inside of the containment 11. Accordingly, the primary cooling water is dispersed to a large amount of steam that occurs in the containment 11, where the cooling water draws a large amount of energy, cools the inside of the containment 11, falls with its temperature thus increased, and is returned to the refueling water storage pits 22 via a collection route. Accordingly, it is possible to draw the energy emitted into the inside of the containment 11 by using the dispersed primary cooling water, and thus integrity of the containment 11 can be maintained.

Furthermore, each of the injection pumps 28 and 30 is driven to send the primary cooling water stored in each of the refueling water storage pits 22 to the low-temperature feeding pipe 15 via each of the cooling water supply lines 27 and 29 or to the PWR 12 via the high-temperature feeding pipe 14. The cooling water then cools the reactor internal 18 of the PWR 12, which makes it possible to inhibit the temperature of the reactor internal 18 from increasing.

As described above, when an accident of a break of the cooling pipe occurs in the nuclear power plant 10, the cooling water in the refueling water storage pits 22 is dispersed from the spray nozzles 25 into the containment 11 and is sent to the PWR 12, which makes it possible to urgently cool the containment 11. When, for example, a cooling pipe breaks, foreign matter, such as fractions of the broken pipe and the insulator of the pipe, is caused, falls into the refueling water storage pits 22, and gets into the cooling water. For this reason, the recirculation sump screen 26 is placed on each of the refueling water storage pits 22 to cover the top of the refueling water storage pit 22. Accordingly, the recirculation sump screen 26 hinders the foreign matter to inhibit the foreign matter from entering the refueling water storage pits 22, which prevents each of the lines 23, 27 and 29 from being damaged due to the foreign matter getting into each of the lines 23, 27 and 29.

The recirculation sump screen 26 consists of, for example, a porous plate and thus is capable of filtering out foreign matter having a large particle diameter but is unable to filter out foreign matter having a small particle diameter and the foreign matter passes through (is not filtered out by) the recirculation sump screen 26. For this reason, when an accident of a break of the cooling pipe occurs, it is necessary to evaluate in advance how much foreign matter passes through the recirculation sump screens 26.

Figure 2:
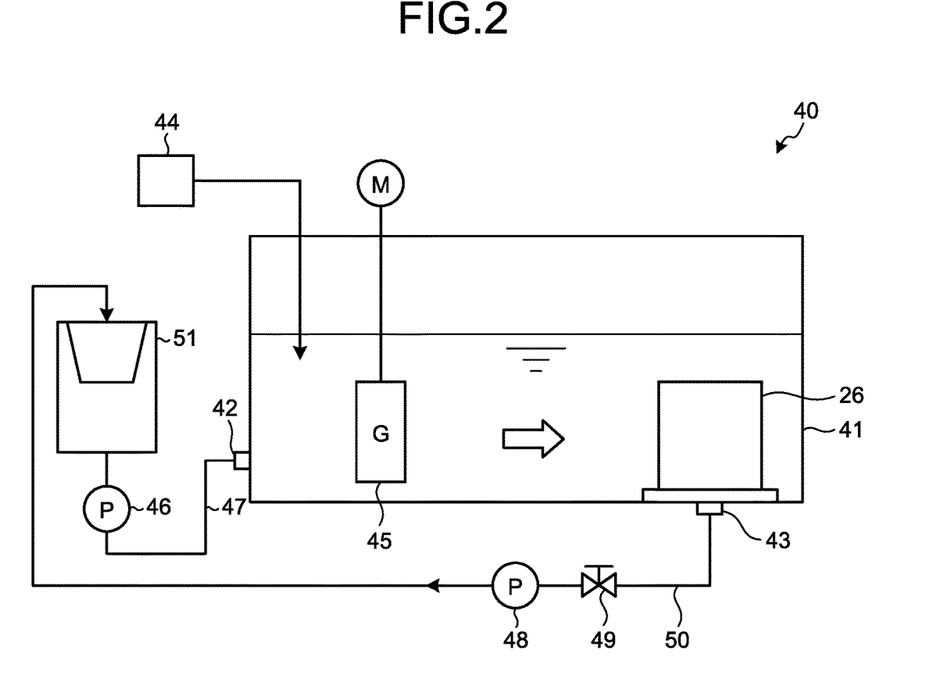
FIG. 2 is a schematic diagram illustrating a testing device for measuring an amount of foreign matter passed through a recirculation sump screen.

FIG. 2 is a schematic diagram representing a testing device for measuring an amount of foreign matter passed through a recirculation sump screen.

As illustrated in FIG. 2, in a testing device 40 for measuring an amount of foreign matter passed through a recirculation sump screen, cooling water can be stored in a test tank 41. A cooling water supply unit 42 is provided on a wall on one end of the test tank 41 and a cooling water discharge unit 43 is provided at the bottom of the other end. In the test tank 41, while a foreign matter inputter 44 and a stirring unit 45 are provided on the side of the cooling water supply unit 42, the recirculation sump screen 26 can be set above the cooling water discharge unit 43 at the bottom on the other end. A cooling water supply line 47 provided with a pump 46 has a tip that is connected to the cooling water supply unit 42. A cooling water discharge line 50 provided with a pump 48 and an open/close valve 49 has a base end that is connected to the cooling water discharge unit 43 and has a tip that is connected to a filter 51. The filter 51 has an outlet port to which the base end of the cooling water supply line 47 is connected.

When each of the pumps 46 and 48 are driven and the open/close valve 49 is opened, the cooling water in the test tank 41 is discharged into the cooling water discharge line 50 through the cooling water discharge unit 43 and is filtered at the filter 51 and then is returned from the cooling water supply line 47 into the test tank 41 through the cooling water supply unit 42. Accordingly, in the test tank 41, a flow of the cooling water from one end to the other end occurs. Here, when foreign matter in a size on which fractions and an insulator of the cooling pipe is assumed is input from the foreign matter inputter 44 and is stirred by the stirring unit 45, the foreign matter input from one end flows to the other end and is filtered out by the recirculation sump screen 26. Foreign matter having a small diameter however passes through the recirculation sump screen 26, is discharged into the cooling water discharge line 50 from the cooling water discharge unit 43, and is filtered out by the filter 51. Measuring the weight of the foreign matter filtered by the filter 51 thus makes it possible to know the amount of foreign matter passed through the recirculation sump screen 26 (passed foreign matter amount).

A method of evaluating an amount of passed foreign matter through a recirculation sump screen of the present embodiment includes acquiring sets of test data on amounts of foreign matter passed through the recirculation sump screen 26 when different amounts of foreign matter are input; forming a passed foreign matter amount approximate line that approximates the amounts of passed foreign matter with respect to the amounts of input foreign matter on the basis of the sets of test data on the amounts of passed foreign matter; forming a passed foreign matter amount envelope tangent to the passed foreign matter amount approximate line; and calculating a total passed foreign matter amount with respect to the amounts of input foreign matter on the basis of the passed foreign matter amount envelope to evaluate the recirculation sump screen 26.

The method of evaluating an amount of foreign matter amount passed through a recirculation sump screen of the present embodiment will be described in detail below.

Figure 3:
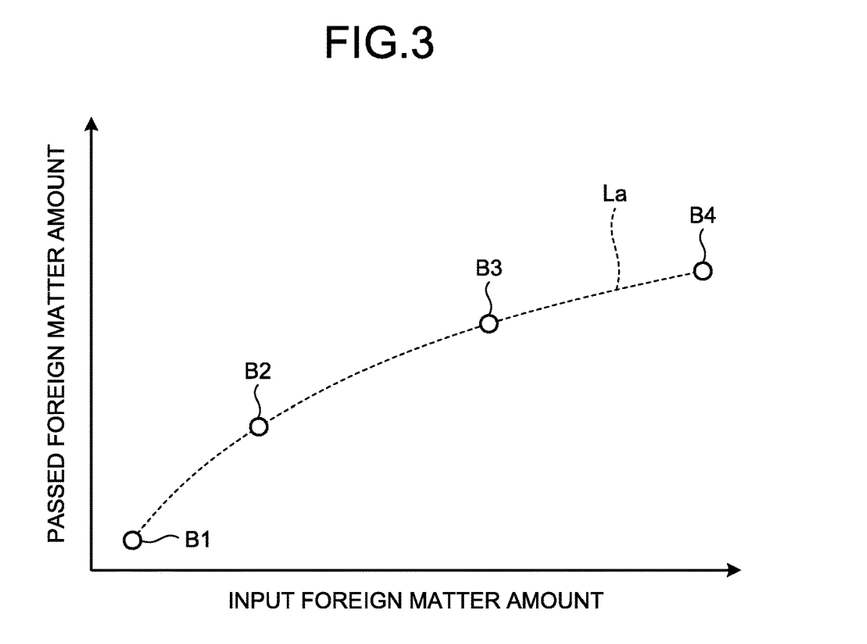
FIG. 3 is a graph for explaining a method of evaluating an amount of foreign matter passed through a recirculation sump screen according to an embodiment, representing a result of measuring amounts of foreign matter passed through a recirculation sump screen.
Figure 4:
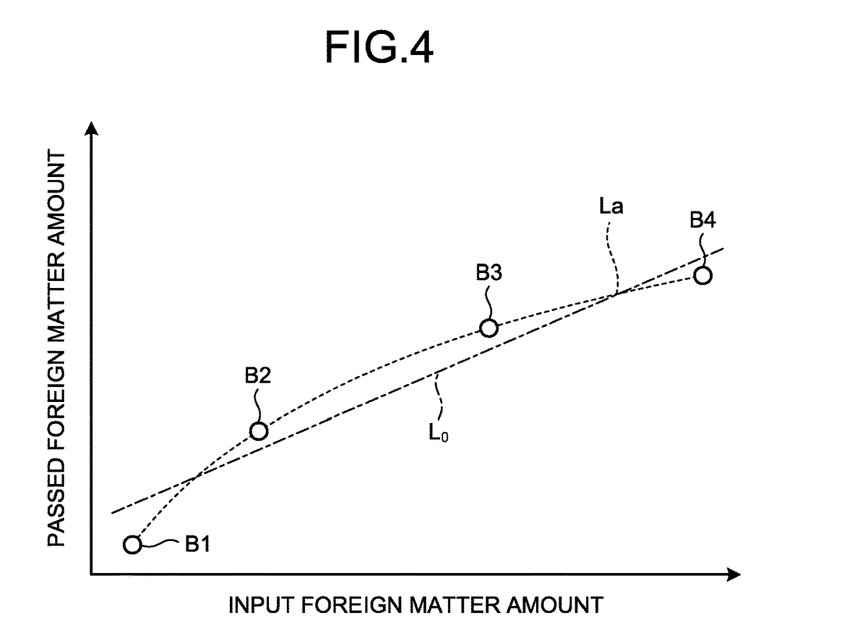
FIG. 4 is a graph for explaining the method of evaluating an amount of foreign matter passed through a recirculation sump screen according to the embodiment, representing an approximate expression of the amounts of foreign matter passed through the recirculation sump screen.
Figure 5:
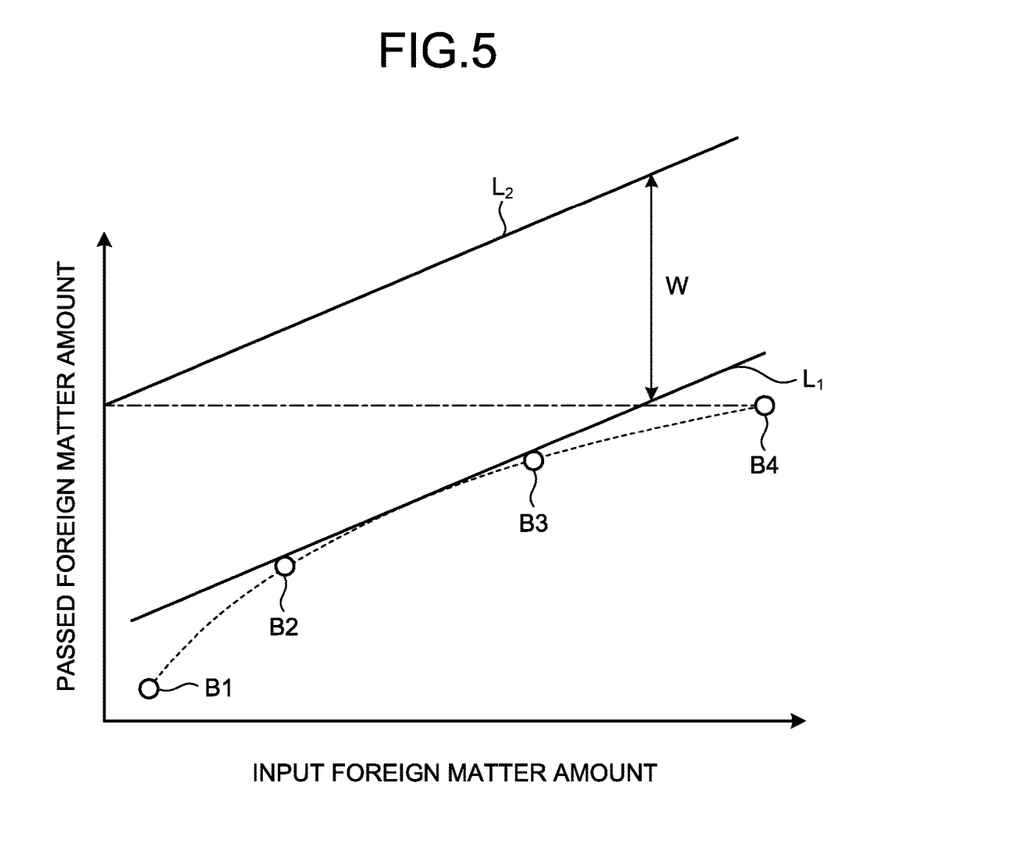
FIG. 5 is a graph for explaining the method of evaluating an amount of foreign matter passed through a recirculation sump screen according to the embodiment, representing a calculated value of the amounts of foreign matter passed through the recirculation sump screen.

FIG. 3 is a graph for explaining the method of evaluating an amount of foreign matter passed through a recirculation sump screen according to the present embodiment, representing a result of measuring amounts of foreign matter passed through a recirculation sump screen. FIG. 4 is represents an approximate expression of the amounts of foreign matter passed through the recirculation sump screen. FIG. 5 represents a calculated value of the amounts of foreign matter passed through the recirculation sump screen.

In the method of evaluating an amount of foreign matter passed through a recirculation sump screen according to the present embodiment, first of all, with the above-described testing device 40, multiple (five in the present embodiments) tests in which the amounts of foreign matter input from the foreign matter inputter 44 are different from one another are carried out, and test data on the amounts of the passed foreign matter is obtained by measuring the amounts of the passed foreign matter passed through the recirculation sump screen 26 when the different amounts of foreign matter are input.

As illustrated in FIG. 3, sets of test data B1, B2, B3 and B4 on the amounts of the passed foreign matter passed through the recirculation sump screen 26 when the different amounts of foreign matter are input are graphed and a passed foreign matter amount approximate line La (dotted line in FIG. 3) that approximates the passed foreign matter amounts with respect to the input foreign matter amounts is formed on the basis of the multiple sets of test data B1, B2, B3 and B4. The passed foreign matter amount approximate line La is a quadratic curve with an upper convex shape, representing that, while the passed foreign matter amount increases with an increase in the amount of input foreign matter, the degree of the increase (amount of change) lowers.

A passed foreign matter amount approximate straight line $L_0$ is then calculated on the basis of the passed foreign matter amount approximate line La. Accordingly, it is possible to obtain the following Equation (1) according to the passed foreign matter amount approximate straight line $L_0$, where L is the amount of input foreign matter and a and b are coefficients associated with the passed foreign matter amount.

$$\text{passed foreign matter amount} = aL + b \tag{1}$$

Furthermore, because the passed foreign matter ratio is a function of the input foreign matter amount L, it is possible to calculate a passed foreign matter amount L·f(L) according to the following equation (2) with the passed foreign matter amount f(L).

$$L \cdot f(L) = aL + b \tag{2}$$

It is possible to calculate a total amount of passed foreign matter according to the following Equation (3) where i(n) is the number of recirculation sump screens 26 (the number of tests).

$$\sum_{i=1}^{n} Lif(Li) = (aL_1 + b) + (aL_2 + b) + (aL_3 + c) + \ldots \tag{3}$$
$$= a(L_1 + L_2 + L_3 + \ldots) + nb$$

The passed foreign matter amounts $L \cdot f(L_1)$, $L \cdot f(L_2)$, $L \cdot f(L_3)$ ... are equal to or smaller than the total input foreign matter amount $L_t$ and therefore it is possible to obtain the following Equation (4).

$$\sum_{i=1}^{n} Lif(Li) \leq a \cdot L_t + nb \tag{4}$$

In other words, as shown in FIG. 4 and FIG. 5, a passed foreign matter amount envelope $L_1$ that is parallel to the passed foreign matter amount approximate straight line $L_0$ and that is tangent to the passed foreign matter amount approximate line La is calculated. The passed foreign matter amount envelope $L_1$ is a primary expression straight line having the same obliqueness as that of the passed foreign matter amount approximate straight line $L_0$.

The passed foreign matter amount envelope $L_1$ is set in an area shifted to a shifted area W moved from a position of tangent of the passed foreign matter amount approximate line La to a pre-set side where the passed foreign matter amount increases. The shifted area W is an area moved to a side where the amount of passed foreign matter is smaller than the maximum value B4 of the sets of test data on the amounts of passed foreign matter. In other words, the shifted area W is an area between the passed foreign matter amount envelope line $L_1$ and a passed foreign matter amount envelope line $L_2$, and the passed foreign matter amount envelope line $L_2$ is set such that its minimum value is the maximum value B4 of the sets of test data on the amounts of passed foreign matte.

The total passed foreign matter amount with respect to the total input foreign matter amount is then calculated on the basis of the passed foreign matter amount envelope line $L_1$ (the passed foreign matter amount envelope $L_1$ to the passed foreign matter amount envelope $L_2$) and the recirculation sump screen 26 is evaluated.

As described above, the method of evaluating an amount of foreign matter passed through a recirculation sump screen according to the present embodiment includes acquiring sets of test data on amounts of foreign matter passed through the recirculation sump screen 26 when different amounts of foreign matter are input; forming a passed foreign matter amount approximate line that approximates the amounts of passed foreign matter with respect to the amounts of input foreign matter on the basis of the sets of test data on the amounts of passed foreign matter; forming a passed foreign matter amount envelope tangent to the passed foreign matter amount approximate line; and calculating a total passed foreign matter amount with respect to the amounts of input foreign matter on the basis of the passed foreign matter amount envelope to evaluate the recirculation sump screen 26.

Accordingly, it is possible to calculate the total passed foreign matter amount easily and evaluate the recirculation sump screen 26 accurately, without individually calculating and evaluating the amounts of foreign matter reaching the multiple recirculation sump screens 26 and the passed foreign matter amounts and without necessity of calculating a ratio of the passed foreign matter.

In the method of evaluating an amount of foreign matter passed through a recirculation sump screen according to the present embodiment, the passed foreign matter amount approximate line is a quadratic curve and the passed foreign matter amount envelope is a primary expression straight line. Accordingly, it is possible to calculate the total amount of passed foreign matter accurately according to one simple formula.

In the method of evaluating an amount of foreign matter passed through a recirculation sump screen according to the present embodiment, the passed foreign matter amount approximate straight line is formed on the basis of the passed foreign matter amount approximate line and the passed foreign matter amount envelope is formed on the basis of the passed foreign matter amount approximate straight line. Calculating the passed foreign matter amount approximate straight line thus makes it possible to calculate an average ratio of the passed foreign matter between the multiple recirculation sump screens according to the obliqueness, which makes it possible to easily calculate the total passed foreign matter amount.

In the method of evaluating an amount of foreign matter passed through a recirculation sump screen according to the present embodiment, a passed foreign matter amount envelope is set in a shifted area defined by the passed foreign matter amount envelope tangent to the passed foreign matter amount approximate line and a passed foreign matter amount envelope shifted to a pre-set side where the passed foreign matter amount increases. Accordingly, it is possible to calculate the total amount of passed foreign matter while a sufficient factor of safety is secured.

In the method of evaluating an amount of foreign matter passed through a recirculation sump screen according to the present embodiment, the shifted area is set in the area moved to a side where the amount of passed foreign matter is smaller than the maximum value of the sets of test data on the amounts of passed foreign matter, and thus the efficiency in processing for calculating the total amount of passed foreign matter can be improved without securing an excessive factor of safety.

In the above-described embodiment, the passed foreign matter amount envelope is a primary expression straight line; however, it may be a quadratic curve.

REFERENCE SIGNS LIST

10 NUCLEAR POWER PLANT
11 CONTAINMENT
12 PRESSURIZED WATER REACTOR
13 STEAM GENERATOR
14 HIGH-TEMPERATURE FEEDING PIPE
15 LOW-TEMPERATURE FEEDING PIPE
17 PRESSURIZER
18 REACTOR INTERNAL
21 REACTOR EMERGENCY COOLING DEVICE
22 REFUELING WATER STORAGE PIT
23 COOLING WATER DISPERSION LINE
24 SPRAY PUMP
25 SPRAY NOZZLE
26 RECIRCULATION SUMP SCREEN
27 LOW-PRESSURE COOLING WATER SUPPLY LINE
28 LOW-PRESSURE INJECTION PUMP
29 HIGH-PRESSURE COOLING WATER SUPPLY LINE
30 HIGH-PRESSURE INJECTION PUMP
31 FUEL REPLACEMENT WATER TANK
32 COOLING WATER SUPPLY LINE
33 STEAM SUPPLY PIPE
34 POWER GENERATION FACILITY
35 CONDENSED WATER RETURN PIPE

The invention claimed is:

1. A testing device, comprising:
a test tank that stores cooling water therein;
a foreign matter inputter that inputs foreign matter to the test tank;
a recirculation sump screen set in the test tank and that filters the foreign matter; and
a processor,
wherein the processor executes a program for evaluating an amount of foreign matter passed through the recirculation sump screen, the program causing the processor to perform:
acquiring sets of test data on amounts of foreign matter passed through a recirculation sump screen when different amounts of the foreign matter are input;
forming a passed foreign matter amount approximate line that approximates the amounts of passed foreign matter with respect to the amounts of input foreign matter on the basis of the sets of test data on the amounts of passed foreign matter;
forming a passed foreign matter amount line tangent to the passed foreign matter amount approximate line; and
calculating a total amount of passed foreign matter with respect to the amounts of input foreign matter on the basis of the passed foreign matter amount line to evaluate the recirculation sump screen.

2. The testing device according to claim 1, wherein the passed foreign matter amount approximate line is a quadratic curve and the passed foreign matter amount line is a primary expression straight line expressed by a function of an input foreign matter amount.

3. The testing device according to claim 2, further comprising forming a passed foreign matter amount approximate straight line on the basis of the passed foreign matter amount approximate line and forming the passed foreign matter amount line on the basis of the passed foreign matter amount approximate straight line.

4. The testing device according to claim 1, wherein a passed foreign matter amount line is set in a length defined by the passed foreign matter amount line tangent to the passed foreign matter amount approximate line and a passed foreign matter amount line shifted to a pre-set side where the passed foreign matter amount increases.

5. The testing device according to claim 4, wherein the length is a length moved to a side where the amount of passed foreign matter is smaller than a maximum value of the sets of test data on the amounts of passed foreign matter.

6. The testing device according to claim 2, wherein a passed foreign matter amount line is set in a length defined by the passed foreign matter amount line tangent to the passed foreign matter amount approximate line and a passed foreign matter amount line shifted to a pre-set side where the passed foreign matter amount increases.

7. The testing device according to claim 3, wherein a passed foreign matter amount line is set in a length defined by the passed foreign matter amount line tangent to the passed foreign matter amount approximate line and a passed foreign matter amount line shifted to a pre-set side where the passed foreign matter amount increases.

\* \* \* \* \*